United States Patent [19]
Allen et al.

[11] Patent Number: 5,567,488
[45] Date of Patent: Oct. 22, 1996

[54] MULTILAYER BARRIER FILM FOR TRANSDERMAL DRUG DELIVERY SYSTEM AND OSTOMY APPLICATIONS

[75] Inventors: Scott I. Allen, Newark; Michael Ferguson, Granville; Harvey Tung, Newark, all of Ohio

[73] Assignee: The Dow Chemical Company, Midland, Mich.

[21] Appl. No.: 216,903

[22] Filed: Mar. 23, 1994

Related U.S. Application Data

[63] Continuation-in-part of Ser. No. 121,474, Sep. 16, 1993, abandoned.

[51] Int. Cl.$^6$ .................................................. B32B 27/32
[52] U.S. Cl. .......................... 428/34.1; 428/483; 428/416; 428/424.2; 428/424.8; 604/332; 604/338; 604/890.1; 424/443; 424/444; 424/445
[58] Field of Search .................... 428/483, 516, 428/34.1, 424.2, 424.8; 604/332, 338, 890.1, 891.1, 892.1; 424/443, 444, 445

[56] References Cited

U.S. PATENT DOCUMENTS 5,271,940  12/1993  Gleary ..................................... 424/448

FOREIGN PATENT DOCUMENTS

| | | |
|---|---|---|
| 240886 | 10/1987 | European Pat. Off. . |
| 318025 | 5/1989 | European Pat. Off. . |
| 366802 | 5/1990 | European Pat. Off. . |
| 435792 | 7/1991 | European Pat. Off. . |
| 524775 | 1/1993 | European Pat. Off. . |
| 274387 | 6/1989 | Germany . |
| 247387 | 12/1989 | Germany . |
| 93/11938 | 6/1993 | WIPO . |

OTHER PUBLICATIONS

Document No. 290014 Date Oct. 1988 Research Disclosure.

*Primary Examiner*—Charles Nold

[57] ABSTRACT

An oxygen and moisture impermeable multilayer barrier film is provided including a barrier layer comprising a homopolymer of vinylidene chloride or a copolymer of vinylidene chloride and vinyl chloride or methyl methacrylate. The barrier layer is coextruded with or laminated to at least one heat sealable skin layer comprising a thermoplastic polyurethane, a substantially linear copolymer of ethylene and an α-olefin, or a homogeneously-branched linear olefin resin to form the barrier film. The multilayer film may be used for reusable ostomy bags, for systems for the transdermal delivery of drugs, and for heat sealable bags used in packaging.

15 Claims, 2 Drawing Sheets

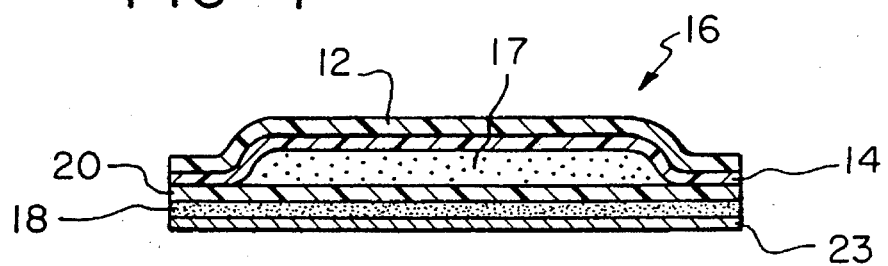
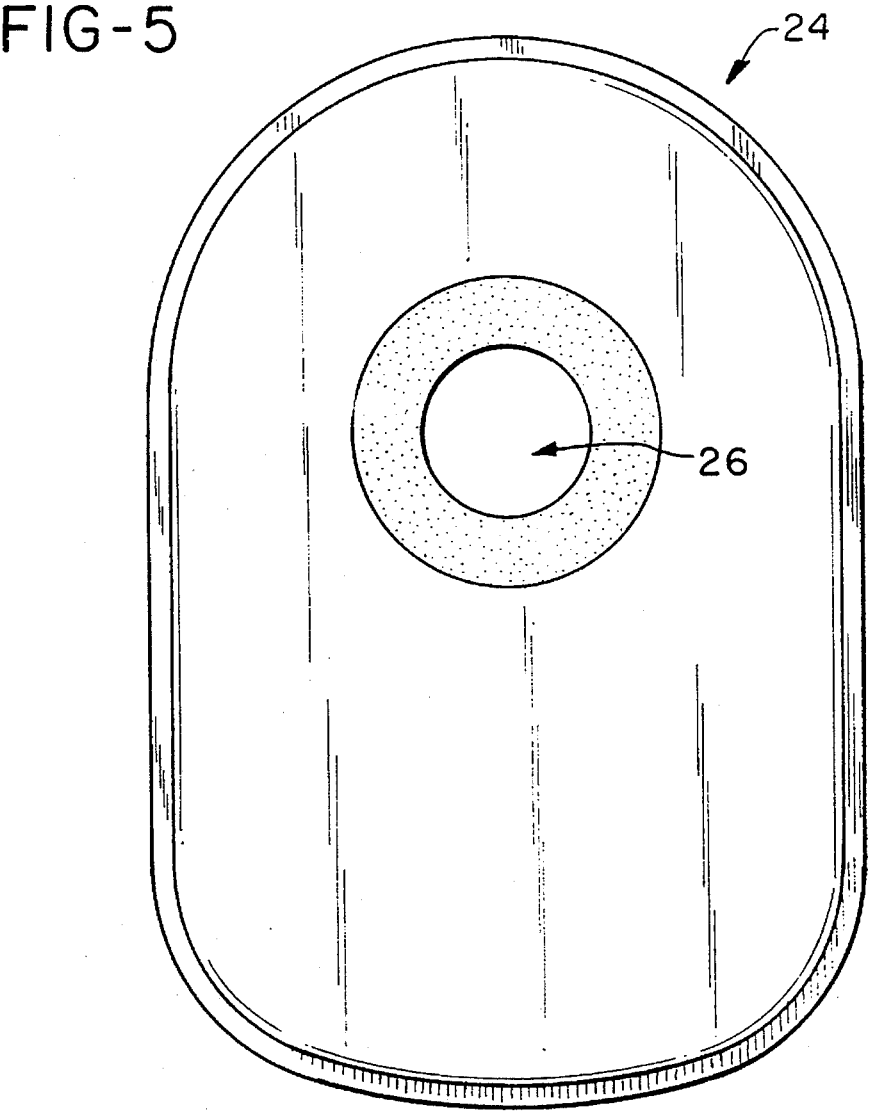

MULTILAYER BARRIER FILM FOR TRANSDERMAL DRUG DELIVERY SYSTEM AND OSTOMY APPLICATIONS

CROSS-REFERENCE TO RELATED APPLICATION

This application is a continuation-in-part of commonly-assigned U.S. patent application Ser. No. 08/121,474, filed Sep. 16, 1993 abandoned.

BACKGROUND OF THE INVENTION

The present invention relates to an oxygen and moisture impermeable multilayer barrier film, and to articles produced therefrom including ostomy bags, laminates for transdermal delivery of drugs, and heat sealable bags.

Plastic film laminates having oxygen and moisture vapor barrier properties are desirable for current packaging requirements, as well as for use in medical applications such as the fabrication of ostomy bags or transdermal drug delivery systems. Such films have been provided through the use of multi-ply film laminates where at least one of the plies is oxygen and moisture vapor impermeable. Typically, the films comprise chlorinated polyethylene films or plasticized polyvinyl chloride films, polyvinylidene chloride copolymer films, or multilayered structures such as ethylene vinyl acetate-polyvinylidene chloride/ethylene vinyl acetate combination films.

Several other methods for producing barrier films have been proposed. For example, Manne et al, U.S. Pat. No. 3,753,828 describes a method of preparing oxygen impermeable film packaging materials using an adhesive-containing Saran resin which is applied to one ply of a two-ply laminate and then cured. However, the process requires the addition of an adhesive and involves curing steps which require the use of a printing press or laminator.

Lustig et al, U.S. Pat. No. 4,348,437 relate to a coextruded multilayer food packaging film comprising a first layer of an ethylene vinyl acetate copolymer, a second layer comprising a polyvinylidene chloride copolymer or an ethylene vinyl alcohol copolymer, and a third layer comprising a blend of a polyurethane polymer and an ethylene vinyl acetate copolymer. However, the film does not provide other desirable physical properties such as softness and low noise characteristics which are required for ostomy applications.

Accordingly, the need still exists for multilayer barrier films which may be produced by simple and inexpensive conventional processes and for films which are impermeable to moisture and oxygen, provide odor barrier, softness, and low noise properties, and which have a heat sealable surface for forming bags or the like.

SUMMARY OF THE INVENTION

The present invention meets that need by providing an oxygen and moisture impermeable multilayer barrier film which may be produced by coextrusion or lamination techniques. The film provides excellent adhesion between layers, odor barrier and softness characteristics, and provides a heat sealable surface for the fabrication of bags.

According to one aspect of the present invention, an oxygen and moisture impermeable multilayer barrier film having a heat seal strength of at least 1.0 lb/inch of film width, and preferably greater than about 1.5 lb/inch of film width, is provided. By "oxygen impermeable", it is meant that the film has an oxygen transmission rate of equal to or less than 90 $cc/m^2/day \cdot atm$. By "moisture impermeable", it is meant that the film has a water vapor transmission rate of equal to or less than about 5 $gm/m^2/day$.

In one embodiment, the film comprises a barrier layer with at least one heat sealable skin layer thereon. The barrier layer comprises, for example, any suitable barrier layer material which will provide the desired oxygen and moisture impermeability while being compatible with the heat sealable skin layer or layers. A preferred barrier material is a copolymer of vinylidene chloride with vinyl chloride or methyl methacrylate. Where the barrier layer includes a copolymer of vinylidene chloride with vinyl chloride or methyl methacrylate, the barrier layer may also optionally include from 0 to 6% by weight of a copolymer of ethylene and vinyl acetate, and more preferably from 4–6% as a processing aid.

In one embodiment of the invention, the barrier layer is coextruded with at least one heat sealable skin layer. To provide the desired softness characteristics, the heat sealable skin layer preferably has a 2% secant modulus of less than about 15,000 psi in both the machine (MD) and transverse (TD) directions. The heat sealable skin layer preferably comprises either a thermoplastic polyurethane, a substantially linear copolymer of ethylene and an α-olefin having a density in the range of from about 0.87–0.92, or a homogeneously-branched linear polyolefin resin. To aid in processing of the film, the skin layer or layers may contain from 0 to 10% by weight of a copolymer of ethylene and vinyl acetate, and more preferably, from 0.5–5% of the copolymer as a processing aid. In addition, the skin layer may optionally contain from about 0.5 to 6% by weight of a slip additive/antiblocking agent package. Where the skin layer is a substantially linear copolymer of ethylene and an α-olefin, it may be desirable to coextrude an adhesive tie layer of a copolymer of ethylene and vinyl acetate between the skin and barrier layers to improve adhesion of those layers.

In a preferred embodiment of the invention, the barrier layer is coextruded between two heat sealable skin layers, where the skin layers comprise about 70% by volume (thickness) of the film and the barrier layer comprises about 30% by volume (thickness) of the film. This construction may be used to form reusable ostomy bags or pouches. The barrier and skin layer or layers may also be formed separately and then laminated together using suitable adhesive polymers, liquid adhesives, or hot melt adhesives. The multilayer barrier films of the present invention exhibit a noise of less than about 85 dB when subjected to flexing through a 65° angle at 0.45 Hz, preferably exhibit a noise of less than about 83 dB when subjected to flexing through a 65° angle at 0.45 Hz, and most preferably exhibit a noise of less than about 81 dB when subjected to flexing through a 65° angle at 0.45 Hz.

In another embodiment of the invention, additional layers may be added to the barrier film to form a system for transdermal delivery of drugs. The system preferably comprises a backing layer of the barrier film which functions as a barrier to the drug system. An adhesive containing an active drug is preferably adhered to one surface of the film. Adjacent the adhesive is a controlled release membrane which is adapted to contact a patient's skin and to controllably release the drug.

In another form of this embodiment, the backing layer may form a reservoir for containing the active drug with the controlled release membrane covering the opening of the reservoir to control the diffusion of the drug into a patient's skin. A peripheral or overall adhesive may be used to adhere the transdermal delivery system to a patient's skin. Preferably, a release liner overlies the adhesive and membrane to protect the construction prior to use.

Accordingly, it is a feature of the present invention to provide an oxygen and moisture impermeable multilayer barrier film which may be produced using coextrusion or lamination processes. Further features of the invention include odor barrier, softness, and low noise properties. Additionally, a heat sealable surface for use in forming bags and pouches is provided. These, and other features and advantages of the present invention will become apparent from the following detailed description, the accompanying drawings, and the appended claims.

BRIEF DESCRIPTION OF THE DRAWINGS

FIG. 4 is a schematic cross-section of another embodiment of a transdermal drug delivery system in accordance with the present invention; and FIG. 5 is a front elevational view of an ostomy bag or pouch formed from the multilayer barrier film of FIGS. 1 or 2 of the present invention.

DETAILED DESCRIPTION OF THE PREFERRED EMBODIMENTS

In one embodiment, the multilayer barrier film of the present invention may be produced using standard extrusion techniques such as feedblock coextrusion, multi-manifold die coextrusion, or combinations of the two. The volume (thickness) of each individual layer may be controlled as it is extruded. Thus, the overall thickness of the multilayer structure may be controlled. Alternatively, the individual layers may be formed separately and laminated together using suitable adhesive bonding layers.

The polymers in the films are not intentionally stretched or oriented other than as a natural consequence of their manufacture to preserve their low noise characteristics. For example, films produced by a blown process will inherently have some orientation in both the machine (MD) and transverse (TD) directions, while cast films will remain unoriented in the transverse direction. Generally, the less orientation which is introduced into the films, the less noisy they will be. The multilayer barrier films of the present invention exhibit a noise of less than about 85 dB when subjected to flexing through a 65° angle at 0.45 Hz, preferably exhibit a noise of less than about 83 dB when subjected to flexing through a 65° angle at 0.45 Hz, and most preferably exhibit a noise of less than about 81 dB when subjected to flexing through a 65° angle at 0.45 Hz Additionally, to provide the desired softness characteristics, the heat sealable skin layer preferably has a 2% secant modulus of less than about 15,000 psi in both the machine (MD) and transverse (TD) directions. 2% secant modulus is a measure of the stiffness or softness of a film. We have found that the lower the value for 2% secant modulus for the heat sealable skin layer, the softer the resulting film will be. Generally, it is desirable for the 2% secant modulus of the film to be as low as possible and yet still remain processable by conventional equipment. For the overall multilayer film, it is preferable that the 2% secant modulus be 30,000 psi or below. The resulting multilayer films possess low oxygen and vapor transmission rates, as well as having the odor barrier, softness, and low noise properties needed for ostomy applications.

Figure 1:
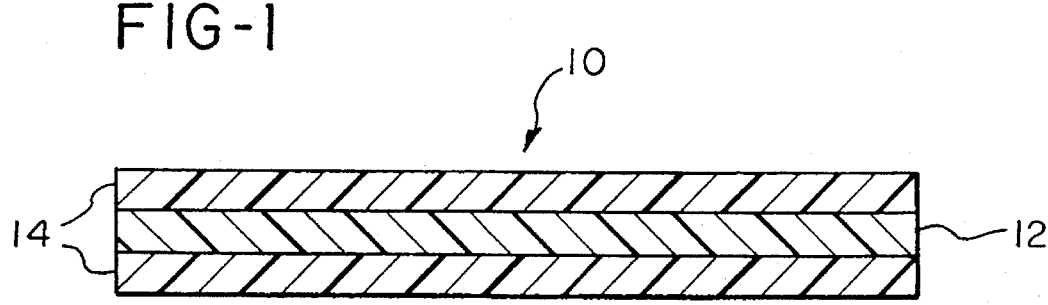
FIG. 1 is a schematic cross-section of one embodiment of the multilayer barrier film of the present invention.

Referring now to FIG. 1, an oxygen and moisture impermeable multilayer barrier film 10 is illustrated. The film 10 includes a barrier layer 12 which may be of a copolymer of vinyl chloride (15–20% by weight) and vinylidene chloride (80–85% by weight) or a copolymer of vinylidene chloride (93–94% by weight) and methyl methacrylate (6–7% by weight). Examples of suitable barrier materials include Saran® 469 and Saran® MA, commercially available from The Dow Chemical Company. Where a Saran® barrier layer material is used, the barrier layer may also include from 0 to 6% by weight of a copolymer of ethylene and vinyl acetate, and more preferably from 4–6% by weight of the copolymer as a processing aid. A suitable class of ethylene/vinyl acetate copolymer compositions are those copolymers sold commercially as Elvax® resins by E. I. du Pont de Nemours & Co., Inc.

As shown, the barrier layer is preferably coextruded with or laminated between two heat sealable skin layers 14 comprising either a thermoplastic polyurethane, a substantially linear copolymer of ethylene and an $\alpha$-olefin having a density in the range of from about 0.87–0.92 gm/cc, or a homogeneously-branched linear polyolefin resin. Suitable thermoplastic polyurethanes include those based on the reaction of a polyisocyanate (aromatic or aliphatic) with polyester, polyether, or polycaprolactone polyols. Chain extenders such as diols and diamines may also be used in the reaction. Such thermoplastic polyurethanes are commercially available from the B. F. Goodrich Co. under the trademark Estane® and from The Dow Chemical Company under the trademark Pellathane®. A preferred thermoplastic polyurethane composition is Pellathane® 2355-95AE.

To aid in processing of the thermoplastic polyurethane skin layers, the skin layers may contain from 0 to 10% by weight of a copolymer of ethylene and vinyl acetate, and more preferably, from 0.5–5% by weight. In addition, the skin layers may contain from about 0.5–6% by weight of a slip additive and/or antiblocking agent such as Akzo 16LB15, commercially available from Akzo Chemicals Inc. The thermoplastic polyurethane skin layers used in the present invention typically will provide a heat seal strength in the range of from about 7 to 9 lb/inch of film width (measured in accordance with ASTM D 903).

A suitable substantially linear copolymer resin of ethylene and an $\alpha$-olefin is taught in commonly-assigned published PCT application PCT/US92/08812, published Apr. 27, 1993, the disclosure of which is hereby incorporated by reference. These copolymer resins are commercially available from The Dow Chemical Company as polymer resins made using Insite™ constrained geometry catalyst technology (CGCT). The constrained geometry catalysts are described in commonly-assigned copending U.S. application Ser. Nos. 545, 403, filed Jul. 3, 1990 and 758,654, filed Sep. 12, 1991, now U.S. Pat. No. 5,312,380. The catalysts may be generally characterized as comprising a metal coordination complex of a metal of Groups 3–10 or the Lanthanide series of the Periodic Table of Elements and a delocalized $\alpha$-bonded moiety substituted with a constrain-inducing moiety.

Such substantially linear copolymers have the strength and toughness of linear low density polyethylene (LLDPE) but with processability similar to highly branched low density polyethylene (LDPE). Thus, the polymers have processing indices (PI's) less than or equal to 70% of those of a comparable linear olefin polymer and a critical shear rate at onset of surface melt fracture of at least 50% greater than the critical shear rate at onset of surface melt fracture of a traditional linear olefin polymer at about the same $I_2$ and $M_w/M_n$, where $I_2$ is the melt index measured according to ASTM D-1238, Condition 190° C./2.16 kg (formerly known as "Condition E"), $M_w$ is the weight average molecular weight, and $M_n$ is the number average molecular weight of the polymer. The substantially linear copolymers will have from about 0.01 to 3 long chain branches/1000 carbon atoms along the polymer backbone, where long chains are defined as a chain length of at least 6 carbon atoms. The substantially linear copolymers also have homogeneous branching distributions. Copolymers having homogeneous branching distributions are those in which the comonomer is randomly distributed within a given molecule and wherein all the copolymer molecules have the same ethylene/comonomer ratio, as described in U.S. Pat. No. 3,645,992, to Elston, the disclosure of which is incorporated herein by reference.

Moreover, these substantially linear copolymers have desirable quietness for use in ostomy applications. Such substantially linear ethylene/α-olefin copolymers typically will provide a heat seal strength in the range of from about 2 to 3 lb/inch of film width (ASTM D 903). Thus, these substantially linear copolymers are preferred for use in the present invention because they possess a unique combination of processability, quietness, and heat seal strength.

A suitable homogeneously-branched linear polyolefin resin is commercially available from Exxon Corporation under the trademark Exact® or from Mitsui Chemical Co. under the trademark Tafmer®. These resins also provide good heat seal strength and have desirable quietness properties.

The barrier film 10 may be used to form a reusable ostomy bag or pouch by folding the film and heat sealing either the thermoplastic polyurethane, substantially linear ethylene/α-olefin copolymer, or homogeneously-branched linear polyolefin resin skin layers to each other. Preferably, the bag will have an oxygen permeability of less than about 90 cc/m²/day·atm (1.8 cc/100 in²/day·atm). The barrier film 10 may have a total thickness of between about 35 and 100 micrometers, with the barrier layer 12 making up from about 10 to 30% of the total thickness of the film. The skin layers (and adhesive layers, if needed) will typically make up about 70 to 90% of the total thickness of the film.

The multilayer barrier films of the present invention may also be formed by lamination techniques using suitable adhesives. For example, the barrier and skin layer or layers may be formed separately and then laminated together using adhesive polymers, liquid adhesives, or hot melt adhesives. Suitable adhesive polymers to bond the barrier and skin layers include, but are not limited to, ethylenically unsaturated copolymers of vinyl acetate, ethyl acrylate, ethyl methacrylate, methyl acrylic acid, acrylic acid, and carbon monoxide. Other examples include ionomers of ethylene and methyl acrylic acid or acrylic acid and grafted anhydride copolymers. Suitable liquid or hot melt adhesives include, but are not limited to, adhesives based on urethanes, copolyesters, and copolymers of amide acrylates.

Figure 2:
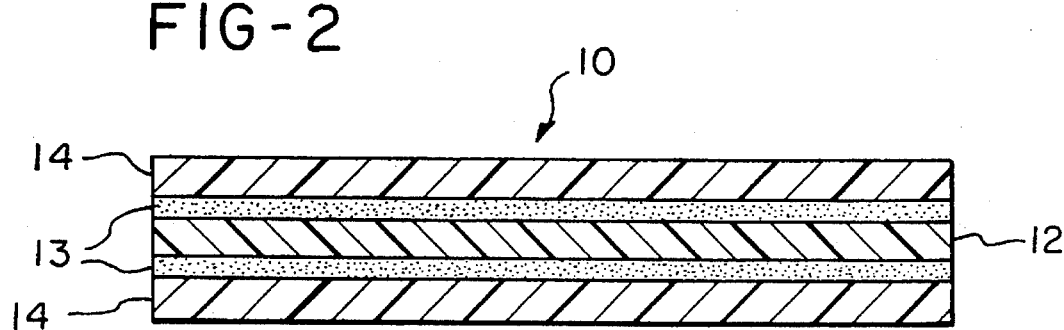
FIG. 2 is a schematic cross-section of another embodiment of the multilayer barrier film of the present invention.

FIG. 2 schematically illustrates a five-layer oxygen and moisture impermeable barrier film 10. The film 10 includes a barrier layer 12 of a suitable barrier material as discussed above. The barrier layer is preferably coextruded with two outer heat sealable skin layers 14 with adhesive layers 13 sandwiched therebetween. The heat sealable skin layers in this five layer embodiment may comprise the substantially linear copolymer of ethylene and an α-olefin of published PCT application No. PCT/US92/08812 or homogeneously branched linear polyolefin resins such as the Exact® and Tafmer® resins. Suitable adhesives for layers 13 include copolymers of ethylene and vinyl acetate which improve the adherence of the barrier and skin layers to each other.

Figure 3:
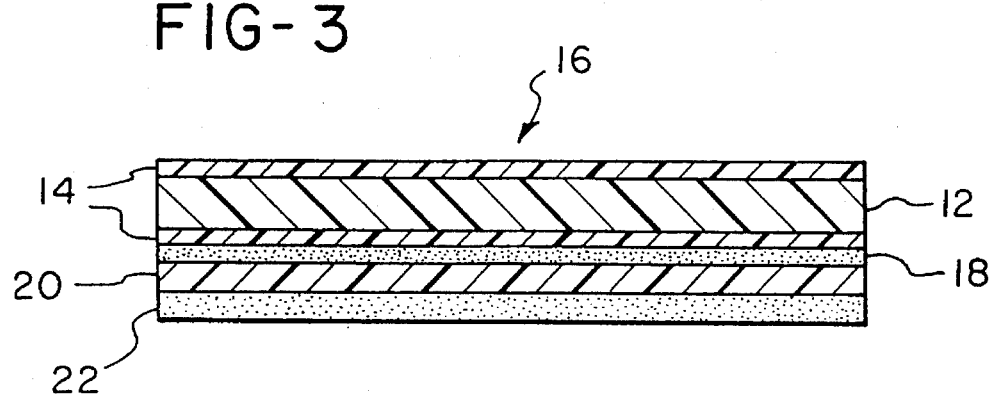
FIG. 3 is a schematic cross-section of one embodiment of a transdermal drug delivery system in accordance with the present invention.

FIG. 3 illustrates another embodiment of the invention in which additional layers are included with the barrier film to form a system 16 for transdermal delivery of drugs. In its simplest form, the barrier layer 12 and skin layers 14 of the film serve as a backing film that is a barrier to the drug system. The barrier film further includes an adhesive layer 18 containing an active drug blended in a matrix therein adhered to one surface of the film. The adhesive which is selected should be compatible with the active drug and permeable to the drug. There are many active drugs which can be administered to a patient in this manner including, for example, estrogen, nitroglycerin, nicotine, and scopolamine. In theory, almost any drug may be administered in this manner.

A controlled release membrane 20 adapted to contact a patient's skin and to controllably release the drug overlies adhesive layer 18. An additional adhesive layer 22, which may be applied peripherally or over the entire surface of membrane 20, may also be present to secure the transdermal delivery system 16 to a patient's skin. The adhesives used in the practice of this embodiment of the invention should be medical grade adhesives such as silicone, acrylic, or vinyl acetate adhesives. Generally, in this embodiment, the system 16 will be sealed in a package or secured to a second barrier film which is removed prior to use.

FIG. 4 illustrates an alternative form of a transdermal drug delivery system 16 in accordance with the present invention. Barrier layer 12 and skin layer 14 form a barrier film which is formed into a reservoir to contain active drug 17 therein. The opening to the reservoir is covered by a controlled release membrane 20. An adhesive 18, which may either be peripherally applied or applied over the entire area of membrane 20, acts to secure system 16 to a patient's skin. Again, the adhesive which is selected should be compatible with the active drug and permeable to the drug. Preferably, a release liner 23 or the like covers and protects the adhesive 18 and membrane 20 prior to use.

FIG. 5 illustrates a typical reusable ostomy bag 24 including an opening 26 formed from the multilayer barrier films of either FIGS. 1 or 2. The bag may be formed by folding and heat sealing the edges of multilayer film 10. The film is preferably folded and sealed such that one heat sealable skin layer provides the inner surface of the bag or pouch 24. The barrier film of the present invention provides softness and quietness features which are desirable for ostomy applications, as well as moisture resistance and odor and oxygen barrier properties. As will be appreciated by those skilled in the art, the barrier films of the present invention may also find use in other packaging applications where moisture and oxygen barrier properties are required.

In order that the invention may be more readily understood, reference is made to the following examples, which are intended to be illustrative of the invention, but are not intended to be limiting in scope.

EXAMPLE 1

A five-layer barrier film was produced in accordance with the present invention and included a core barrier layer, two outer skin layers, and two intermediate tie layers joining the core and outer skin layers together. The layers were coextruded using conventional techniques. The core barrier layer was Saran® 469, commercially available from The Dow Chemical Company and included about 4% by weight of a processing aid (Elvax® 3180 resin available from E. I. du Pont de Nemours & Co., Inc.). The two outer skin layers comprised a thermoplastic polyurethane (Pellathane® 2355-95AE, available from The Dow Chemical Company) which included about 5% by weight of a slip additive (Akzo 16LB15, commercially available from Akzo Chemicals Inc.). The two intermediate tie layers were also a thermoplastic polyurethane (Pellathane® 2355-95AE).

The resulting multilayer barrier film had a thickness of approximately 2.0 mils and an ultimate tensile strength (ASTM D-882) of 12,330 (MD) and 7,492 (TD) psi, respectively. The film had an oxygen transmission rate (ASTM D-3985) of 0.39 cc/100 in$^2$/day·atm and a water vapor transmission rate (Permatran W) of 0.181 gm/100 in$^2$/day. The film also had a 2% secant modulus (ASTM method D-882 using an Instron tensile tester) of 18,450 psi (MD) and 21,180 psi (TD).

EXAMPLE 2

Three different five-layer barrier films were produced in accordance with the present invention, and each film included a core barrier layer, two outer skin layers, and two intermediate tie layers joining the core and outer skin layers together. The layers were coextruded using conventional techniques. The core barrier layer in each instance was Saran® 469, commercially available from The Dow Chemical Company and included about 4% by weight of a processing aid (Elvax® 3180 resin (28% vinyl acetate, 25 melt index) available from E. I. du Pont de Nemours & Co., Inc.). The two outer skin layers comprised the polyolefin resins reported in Table 1 below. The two intermediate tie layers were copolymers of ethylene and vinyl acetate available from Exxon Corp. under the designation Exxon LD 740.16 (23% vinyl acetate, 5 melt index).

The resulting multilayer barrier films had nominal thicknesses of approximately 3.0 mils, with the core layer and tie layers making up approximately 10% of the film thickness and the outer skin layers making up approximately 90%. The films also had a 2% secant modulus (ASTM method D-882 using an Instron tensile tester) as reported below.

These films were tested for quietness by forming a 4"×4" piece of the film into a cylinder and flexing the film through an angle of 65° at a frequency of 0.45 Hz and measuring the sound level in decibels (dB). Data are reported in Table 1 below. The noise levels show the improved quietness for the substantially linear α-olefin polymers (Samples 2 and 3) of the present invention versus conventional low density polyethylene (Sample 1).

TABLE 1

| Sample # | Polymer Resin | Noise (dB) | 2% secant Modulus MD (psi) | TD |
|---|---|---|---|---|
| 1 | Low density polyethylene (0.9245 gm/cc, 1.9 MI) | 89 | 23,000 | 23,000 |
| 2 | Blend of 50% CGCT substantially linear ethylene/α-olefin copolymer (0.909 g/cc, 3.2 MI)/ 50% CGCT substantially linear ethylene/α-olefin copolymer (0.870 g/cc, 1.0 MI) | 81 | 9,500 | 11,000 |
| 3 | Blend of 25% CGCT substantially linear ethylene/α-olefin copolymer (0.909 g/cc, 3.2 MI)/ 75% CGCT substantially linear ethylene/α-olefin copolymer (0.870 g/cc, 1.0 MI) | 81 | 8,600 | 9,000 |

TABLE 1-continued

EXAMPLE 3

Three samples of four-layer barrier films were produced in accordance with the present invention, and each film included a core barrier layer, a tie layer and a seal layer, and an outer skin layer. The layers were coextruded using conventional techniques. The core barrier layer in each instance was Saran® 469, commercially available from The Dow Chemical Company and included about 4% by weight of a processing aid (Elvax® 3180 resin (28% vinyl acetate, 25 meltindex) available from E. I. du Pont de Nemours & Co., Inc.). The outer skin layer comprised the polyolefin resins reported in Table 2 below. The intermediate tie layer and seal layer were copolymers of ethylene and vinyl acetate available from Exxon Corp. under the designation Exxon LD 740.16 (23% vinyl acetate, 5 melt index). The resulting multilayer barrier films had nominal thicknesses of approximately 4.0 mils, with the core layer and tie layer making up approximately 10% of the film thickness. The seal layer represented approximately 20% of the film thickness, while the outer skin layer made up the remainder of the structure.

These films were tested for quietness by forming a 4"×4" piece of the film into a cylinder and flexing the film through an angle of 65° at a frequency of 0.45 Hz and measuring the sound level in decibels (dB). Data are reported in Table 2 below. The noise levels show the improved quietness for the substantially linear α-olefin polymers (Sample 2) of the present invention versus conventional low density polyethylene (Sample 1). Comparable noise levels are shown in comparison to a commercial film with a chlorinated polyethylene resin (Sample 3).

TABLE 2

| Sample # | Polymer Resin | Noise (dB) | 2% secant Modulus MD (psi) | TD |
|---|---|---|---|---|
| 1 | Low density polyethylene (0.925 gm/cc, 1.9 MI) | 86 | 27,000 | 28,000 |
| 2 | Blend of 50% CGCT substantially linear ethylene/α-olefin copolymer (0.909 g/cc, 3.2 MI)/ 50% CGCT substantially linear ethylene/α-olefin copolymer (0.870 g/cc, 1.0 MI) | 81 | 17,000 | 17,000 |
| 3 | Chlorinated polyethylene | 80 | 17,000 | 17,000 |

EXAMPLE 4

To demonstrate the quietness of the skin layers used in the multilayer barrier films of the present invention, a number of monolayer films were prepared using a cast film process. Monolayer films of a thermoplastic polyurethane and a substantially linear ethylene/α-olefin copolymer of the present invention were cast and tested for comparison purposes against prior art chlorinated polyethylene and homogeneously-branched polyethylene films.

The monolayer films were tested for quietness by forming a 4"×4" piece of the film having a 2.0 mil thickness into a cylinder and flexing the film through an angle of 65° at a frequency of 0.45 Hz and measuring the sound level in decibels (dB). Data are reported in Table 3 below. The data show that the films using the thermoplastic polyurethane (Samples 6 and 7) and constrained geometry catalyst technology (CGCT) linear ethylene/α-olefin copolymers (Samples 3–5) of the present invention were at least comparable in quietness to chlorinated polyethylene (Sample 8) and better than other conventional low density polyethylene films (Samples 1 and 2) in commercial use. The films also had a 2% secant modulus (ASTM method D-882 using an Instron tensile tester) as reported below.

TABLE 3

| Sample # (psi) | Polymer Resin | Noise (dB) | 2% secant Modulus MD (psi) | TD |
| --- | --- | --- | --- | --- |
| 1 | Ultra low density polyethylene (Dow Attane ® 4202, 0.912 g/cc, 3.2 MI) | 86 | 16,000 | 16,500 |
| 2 | Linear low density polyethylene (Dow Dowlex ® 2047, 0.917 g/cc, 2.3 MI) | 85 | 18,000 | 18,500 |
| 3 | CGCT substantially linear ethylene/α-olefin copolymer (0.9096 g/cc, 4.7 MI) | 79.5 | 11,500 | 11,500 |
| 4 | CGCT substantially linear ethylene/α-olefin copolymer (0.9015 g/cc, 4.5 MI) | 83.5 | 8,500 | 8,000 |
| 5 | CGCT substantially linear ethylene/α-olefin copolymer (0.8966 g/cc, 1.9 MI) | 80.5 | 6,500 | 6,500 |
| 6 | Thermoplastic polyurethane (Dow Pellathane ® 2355-95AE) | 81.5 | 7,000 | 7,000 |
| 7 | Thermoplastic polyurethane (Dow Pellathane ® 2363-90AE) | 79.5 | 5,000 | 5,000 |
| 8 | Chlorinated polyethylene | 79.5 | 4,000 | 4,000 |

While certain representative embodiments and details have been shown for purposes of illustrating the invention, it will be apparent to those skilled in the art that various changes in the methods and apparatus disclosed herein may be made without departing from the scope of the invention, which is defined in the appended claims.

What is claimed is:

1. An oxygen and moisture impermeable multilayer barrier film having a heat seal strength of at least about 1.0 lb/inch width of said film, said film comprising a barrier layer and at least one heat sealable skin layer, said skin layer comprising a thermoplastic polymer having a 2% secant modulus of less than about 15,000 psi in both the machine and transverse directions, said barrier film exhibiting a noise of less than about 85 dB when subjected to flexing through a 65° angle at 0.45 Hz.

2. The multilayer barrier film of claim 1 wherein said skin layer comprises either a thermoplastic polyurethane, a substantially linear copolymer of ethylene and an α-olefin resin having a density in the range of from about 0.87–0.92 gm/cc and from about 0.01 to 3 long chain branches/1000 carbon atoms along the polymer backbone, or a homogeneously-branched linear olefin resin.

3. The multilayer barrier film of claim 1 wherein said heat sealable skin layer comprises a thermoplastic polyurethane, and said skin layer contains from 0 to 10% by weight of a copolymer of ethylene and vinyl acetate.

4. The multilayer barrier film of claim 1 wherein said barrier layer is selected from the group consisting of a homopolymer of vinylidene chloride, a copolymer of vinylidene chloride with vinyl chloride or methyl methacrylate.

5. The multilayer barrier film of claim 1 wherein said film has an oxygen transmission rate of less than about 90 cc/m²/day·atm.

6. The multilayer barrier film of claim 1 wherein said barrier layer is positioned between two heat sealable skin layers.

7. The multilayer barrier film of claim 6 wherein said skin layers comprise 70% by weight of said film and said moisture barrier layer comprises 30% by weight of said film.

8. The multilayer barrier film of claim 1 wherein said skin layers contain from about 0.5–5% by weight of a slip additive/antiblocking agent package.

9. The multilayer barrier film of claim 3 wherein said skin layers contain from 1–10% by weight of a copolymer of ethylene and vinyl acetate.

10. The multilayer barrier film of claim 1 wherein said skin layer is a substantially linear copolymer of ethylene and an α-olefin having a density in the range of from about 0.87–0.92 gm/cc, from about 0.01 to 3 long chain branches/1000 carbon atoms along the polymer backbone.

11. The multilayer barrier film of claim 10 including an intermediate tie layer of a copolymer of ethylene and vinyl acetate between said barrier layer and said skin layer.

12. The multilayer barrier film of claim 1 wherein said barrier layer comprises a homopolymer of vinylidene chloride or a copolymer of vinylidene chloride with vinyl chloride or methyl methacrylate, and from about 1–6% of a copolymer of ethylene and vinyl acetate.

13. The multilayer barrier film of claim 1 wherein said barrier film further includes:

a) an adhesive containing an active drug adhered to one surface of said barrier film; and b) a controlled release membrane adjacent said adhesive and adapted to controllably release said drug to a patient's skin.

14. The multilayer barrier film of claim 13 further including an adhesive adhered to a least a portion of said controlled release membrane and a release liner overlying said adhesive and release membrane to form a system for transdermal delivery of drugs.

15. The multilayer barrier film of claim 1 wherein said at least one skin layer is heat sealed along its edges to form a bag or pouch.

* * * * *